United States Patent
Gagnon

(10) Patent No.: US 9,938,317 B2
(45) Date of Patent: *Apr. 10, 2018

(54) ENHANCED PURIFICATION OF ANTIBODIES AND ANTIBODY FRAGMENTS BY APATITE CHROMATOGRAPHY

(71) Applicant: Bio-Rad Laboratories, Inc., Hercules, CA (US)

(72) Inventor: Peter S. Gagnon, Singapore (SG)

(73) Assignee: Bio-Rad Laboratories, Inc., Hercules, CA (US)

(*) Notice: Subject to any disclaimer, the term of this patent is extended or adjusted under 35 U.S.C. 154(b) by 214 days.

This patent is subject to a terminal disclaimer.

(21) Appl. No.: 14/819,334

(22) Filed: Aug. 5, 2015

(65) Prior Publication Data

US 2015/0353598 A1    Dec. 10, 2015

Related U.S. Application Data

(62) Division of application No. 13/310,576, filed on Dec. 2, 2011, now Pat. No. 9,127,042, which is a division of application No. 12/355,665, filed on Jan. 16, 2009, now Pat. No. 8,093,364.

(60) Provisional application No. 61/011,513, filed on Jan. 18, 2008, provisional application No. 61/069,859, filed on Mar. 19, 2008, provisional application No. 61/070,841, filed on Mar. 27, 2008, provisional application No. 61/135,787, filed on Jul. 24, 2008, provisional application No. 61/189,467, filed on Aug. 20, 2008, provisional application No. 61/062,663, filed on Jan. 28, 2008.

(51) Int. Cl.
    *C07K 1/18* (2006.01)
    *C07K 1/16* (2006.01)

(52) U.S. Cl.
    CPC ............... *C07K 1/18* (2013.01); *C07K 1/16* (2013.01); *C07K 1/165* (2013.01)

(58) Field of Classification Search
    None
    See application file for complete search history.

(56) References Cited

U.S. PATENT DOCUMENTS

| | | | |
|---|---|---|---|
| 4,798,886 A * | 1/1989 | Kato | C07K 1/16 435/183 |
| 5,141,863 A | 8/1992 | Suzuki et al. | |
| 5,441,635 A | 8/1995 | Ichitsuka et al. | |
| 5,843,731 A | 12/1998 | Yamamoto | |
| 7,691,980 B2 | 4/2010 | Gagnon | |
| 7,939,643 B2 * | 5/2011 | Kretschmar | C07K 14/745 530/350 |
| 7,999,085 B2 | 8/2011 | Gagnon | |
| 8,067,182 B2 | 11/2011 | Kelley et al. | |
| 8,093,364 B2 * | 1/2012 | Gagnon | C07K 1/18 424/177.1 |
| 2003/0166869 A1 | 9/2003 | Vedantham et al. | |
| 2006/0165660 A1 | 7/2006 | Kuhne | |
| 2006/0246544 A1 | 11/2006 | Kang et al. | |
| 2007/0293420 A1 | 12/2007 | Schumann et al. | |

FOREIGN PATENT DOCUMENTS

| | | | | |
|---|---|---|---|---|
| EP | 0 256 836 A1 | 2/1988 | | |
| EP | 1 081 221 A1 | 3/2001 | | |
| WO | 89/12678 A1 | 12/1989 | | |
| WO | 2003/059935 A2 | 7/2003 | | |
| WO | 2005/121173 A1 | 12/2005 | | |
| WO | 2006/099308 A2 | 9/2006 | | |
| WO | WO 2009017491 A1 * | 2/2009 | ............... C07K 1/18 | |

OTHER PUBLICATIONS

Arakawa et al. "Solvent modulation of column chromatography" Protein & Peptide Letters, 2008, 15, 544-555.*
Gagnon, "nonionic polymer enhancement of aggregate removal in ion exchange and hydroxyapatite chromatography" 12th Annual Watershide Conference, San Juan, Puerto Rico, Apr. 23-25, 2007, pp. 1-36.*
Gorbunoff et al. "The interaction of proteins with hydroxyapatite III. Mechanism" Analytical Biochemistry 136, 440-445 (1984).*
Arakawa et al.; "Induced binding of proteins by ammonium sulfite in affinity and ion-exchange column chromatography"; *J. Biochem. Biophys. Methods;* 70:493-498 (2007).
Bio-Rad Tech Note 5709—chromatography—"How CHT™ Ceramic Hydroxyapatite Works" 2006, 4 pages.
Bowles et al.; "Large Scale Production and Purification of Paraquat and Desipramine Monoclonal Antibodies and Their FAB Fragments"; *Int. J. Immunopharmac.;* 10(5):537-545 (1988).
Cai et al., "Microcalorimetric studies on the adsorption of DNA by soil colloidal particles"; *Colloids and Surfaces B: Biointerfaces;* 49: 49-54 (2006).
Chang Bioscience—DNA/RNA/Protein/Chemical Molecular Weight Calculator www.changbioscience.com/genetics/mw.html (accessed on Jan. 11, 2011).
International Search Report from PCT/US2009/031293, dated Jun. 9, 2009.
International Search Report from PCT/US2009/031298, dated Jul. 6, 2009.
Notice of Allowance from U.S. Appl. No. 12/355,665 dated Jun. 17, 2011 (3 pages).
Notice of Allowance from U.S. Appl. No. 12/355,665 dated Sep. 13, 2011 (3 pages).
Office Action from U.S. Appl. No. 12/355,665, dated Aug. 23, 2010 (5 pages).
Office Action from U.S. Appl. No. 12/355,665, dated Jan. 25, 2011 (8 pages).
Office Action from U.S. Appl. No. 12/355,686, dated Apr. 26, 2013 (19 pages).

(Continued)

*Primary Examiner* — Daniel E Kolker
*Assistant Examiner* — James L Rogers
(74) *Attorney, Agent, or Firm* — Kilpatrick Townsend and Stockton LLP

(57) ABSTRACT

Methods are disclosed for use of apatite chromatography, particularly without reliance upon phosphate gradients, for purification or separation of at least one intact non-aggregated antibody, or at least one immunoreactive antibody fragment, from an impure preparation. Integration of such methods into multi-step procedures with other fractionation methods are additionally disclosed.

15 Claims, No Drawings

(56) References Cited

OTHER PUBLICATIONS

Office Action from U.S. Appl. No. 12/355,686, dated Aug. 29, 2012 (37 pages).
Office Action from U.S. Appl. No. 12/355,686, dated Jan. 25, 2011 (13 pages).
Office Action from U.S. Appl. No. 12/355,686, dated Jul. 18, 2011 (17 pages).
Office Action from U.S. Appl. No. 12/355,686, dated Mar. 29, 2012 (30 pages).
Office Action from U.S. Appl. No. 12/355,686, dated Nov. 10, 2011 (12 pages).
Search/Examination Report dated Apr. 29, 2011 from European Patent Application No. 10178843.8, 22 pages.
U.S. Appl. No. 12/355,665, filed Jan. 16, 2009 (33 pages).
U.S. Appl. No. 12/355,686, filed Jan. 16, 2009 (29 pages).
U.S. Appl. No. 12/422,141, filed Apr. 10, 2009 (38 pages).
Erythropoeitin pI MW (last viewed Aug. 20, 2012) 1 page.
Gagnon et al.; "A Ceramic Hydroxyapatite-Based Purification Platform Simultaneous Removal of Leached Protein A, Aggregates, DNA, and Endotoxins from MAbs"; *BioProcess International*, 4(2):50-52, 54, 56, 58, 60 (Feb. 2006).
Gagnon et al.; "New Insights into IgG Binding and Aggregate Removal with Hydroxyapatite"; $8^{th}$ *Ube International Bioseparation Symposium;* Nov. 29-31, 2008 (18 pages) (PSG-081121 www.validated.com).
Gagnon et al.; "New Opportunities for Managing DNA with CHT Ceramic Hydroxyapatite and CFT Ceramic Fluoroapatite"; *BioProcess International;* 3(7):52,54 (Jul.-Aug. 2005).
Gagnon et al.; "Practical Issues in the industrial use of hydroxyapatite for purification of monoclonal antibodies"; BIO 322, Poster Session 232nd ACS National Meeting, San Francisco, CA, Sep. 10-14, 2006, 36 pages.
Gagnon et al.; "Phosphate-Free Buffer Systems a New Frontier for Apatite Chromatography"; $4^{th}$ International Conference on Hydroxyapatite, Sonoma, May 4-6, 2008 (36 pages) (PSG-080503 www.validated.com).
Gagnon et al; "Multiple Modes of Aggregate Removal by Hydroxyapatite"; $4^{th}$ International Conference on Hydroxyapatite, Sonoma, May 4-6, 2008 (36 pages) (PSG-080425 www.validated.com).
Gagnon et al; "Reverse Calcium Affinity Purification of Fab with Calcium Derivatized Hydroxyapatite"; *J. Immunol. Methods;* Manuscript Ref. No. JIM-D-0800300; Revised Nov. 20, 2008 (11 pages).
Gagnon, Pete; "Monoclonal antibody purification with hydroxyapatite"; 2009, *New Biotechnology,* vol. 25, No. 5, pp. 287-293.
Gagnon, Peter et al.; "Multiple Modes of Fab Purification with Hydroxyapatite"; Oct. 22, 2008, *BioProcess International Conference,* Asia/Pacific, Mumbai, 28 pages.
Giovannini et al.; "Comparison of different types of ceramic hydroxyapatite for the chromatographic separation of plasmid DNA and a recombinant anti-Rhesus D antibody"; *Bioseparation;* 9:359-368 (2001).
Gooding et al.; "Ion selectivity in the high-performance cation-exchange chromatography of proteins"; *Journal of Chromatography;* 296:321-328 (1984).
Gorbunoff et al.; "Protein Chromatography on Hydroxyapatite Columns"; *Meth. Enzymol.;* 117:370-380 (1985).
Gorbunoff et al.; "The Interaction of Proteins with Hydroxyapatite, I. Role of Protein Charge and Structure"; *Analytical Biochemistry;* 136:425-432 (1984).
Gorbunoff et al.; "The Interaction of Proteins with Hydroxyapatite, II. Role of Acidic and Basic Groups"; *Analytical Biochemistry;* 136:433-439 (1984).
Gorbunoff et al.; "The Interaction of Proteins with Hydroxyapatite, III. Mechanism"; *Analytical Biochemistry;* 136:440-445 (1984).
Guerrier et al.; "A dual-mode approach to the selective separation of antibodies and their fragments"; *Journal of Chromatography B;* 755:37-46 (2001).
Hakamatsuka, Takashi et al.; "Purification of 2-Hydroxyisoflavanone Dehydratase from the Cell Cultures of *Pueraria lobata*"; 1998, *Phytochemistry,* vol. 49, No. 2, pp. 497-505.
Holland et al.; "Purification and characterization of aspartic β-semialdehyde dehydrogenase from yeast and purification of an isoenzyme of glyceraldehyde 3-phosphate dehydrogenase"; 1973, *Biochemistry,* vol. 12, No. 12, pp. 2264-2270.
Karlsson et al.; *Protein Purification: Principles, High Resolution Methods, and Applications.* Chapter 4—Ion Exchange Chromatography, pp. 107-148. $1^{st}$ Edition. Eds. Jansson and Rydén. 1989.
Kawasaki et al.; "Hydroxyapatite high-performance liquid chromatography column performance for proteins"; *Eur. J. Biochem.;* 152:361-371 (1985).
Kawasaki; "Hydroxyapatite as liquid chromatographic packing"; *Journal of Chromatography;* 544:147-184; (1991).
Kopaciewicz et al.; "Retention Model for High-Performance Ion-Exchange Chromatography"; *Journal of Chromatography;* 266:3-21 (1983).
Lasne et al.; "Detection of isoelectric profiles of erythropoietin in urine: differentiation of natural and administered recombinant hormones"; *Analytical Biochemistry;* 311:119-126 (2002).
Leicht et al.; "Large-scale purification of halophilic enzymes by salting-out mediated chromatography"; *Analytical Biochemistry;* 114:186-192 (1981).
Mevarech et al.; "Hydrophobic chromatography and fractionation of enzymes from extremely halophilic bacteria using decreasing concentration gradients of ammonium sulfate"; *Biochemistry;* 15(11):2383-2387 (1976).
Moriya et al.; "Yak1 p, a DYRK family kinase, translocates to the nucleus and phosphorylates yeast Pop2p in response to a glucose signal"; *Genes & Development;* 15:1217-1228 (2001).
Papanikolau et al.; "Application of the effects of ionic strength reducing agent in the purification and crystallization of chitinase A"; *Acta Cryst.;* D58:1593-1596 (2002).
Rounds et al.; "Evaluation of a retention model for high-performance ion-exchange chromatography suing two different displacing salts"; *Journal of Chromatography;* 283:37-45 (1984).
Sun et al.; "Phosphorylated serine 28 of histone H3 is associated with destabilized nucleosomes in transcribed chromatin"; *Nucl. Acids Res.;* 35(19):6640-6647 (2007).
Office Action from U.S. Appl. No. 13/310,576, dated Jul. 31, 2012.
Final Office Action from U.S. Appl. No. 13/310,576, dated Jan. 30, 2013.
Office Action from U.S. Appl. No. 13/310,576, dated Sep. 26, 2014.
Final Office Action from U.S. Appl. No. 13/310,576, dated Feb. 20, 2015.
Office Action from U.S. Appl. No. 12/355,686, dated Jun. 17, 2014.

* cited by examiner

ENHANCED PURIFICATION OF ANTIBODIES AND ANTIBODY FRAGMENTS BY APATITE CHROMATOGRAPHY

RELATED APPLICATIONS

This application is a divisional application of U.S. patent application Ser. No. 13/310,576, filed on Dec. 2, 2011, which is a divisional of U.S. patent application Ser. No. 12/355,665, filed Jan. 16, 2009, now U.S. Pat. No. 8,093,364, which claims priority to U.S. provisional application Ser. No. 61/011,513 filed Jan. 18, 2008; 61/062,663 filed Jan. 28, 2008; 61/069,859 filed Mar. 19, 2008; 61/070,841 filed Mar. 27, 2008; 61/135,787 filed Jul. 24, 2008; 61/189,467 filed Aug. 20, 2008, each of which are expressly incorporated herein by reference in their entireties.

FIELD OF THE INVENTION

This invention relates in certain embodiments to methods for enhancing purification of antibodies and immunoreactive antibody fragments by apatite chromatography in the presence of one or more of borate compounds, sulfate compounds, monocarboxylate compounds, and/or in the presence of calcium compounds. In certain embodiments, the invention may permit more effective separation of intact non-aggregated antibody from unwanted fragments, aggregated antibody, and other contaminants. In other embodiments, the invention may permit more effective purification of immunoreactive antibody fragments. In these or other embodiments, the invention may improve pH control during the separation.

BACKGROUND OF THE INVENTION

Hydroxyapatite [HA] is a crystalline mineral of calcium phosphate with a structural formula of $Ca_{10}(PO_4)_6(OH)_2$. Fluorapatite may be prepared by fluoridating hydroxyapatite, creating a mineral with the structural formula $Ca_{10}(PO_4)_6F_2$. Protein-reactive sites on both minerals include pairs of positively charged calcium ions (C-sites) and triplets of negatively charged phosphate groups (P-sites). C-sites interact with proteins via HA calcium chelation by protein carboxyl clusters. C-sites interact with phosphorylated solutes such as DNA, endotoxin, phosphoproteins, and lipid enveloped viruses via HA calcium coordination by solute phosphate residues. Calcium chelation and coordination are sometimes referred to as calcium affinity. P-sites interact with proteins via phosphoryl cation exchange with positively charged protein amino acid residues (Gorbunoff, *Analytical Biochemistry* 136 425 (1984); Kawasaki, *J. Chromatography* 152 361 (1985)). Hydroxyapatite is most commonly eluted with phosphate gradients. The strong calcium affinity of phosphate suspends calcium chelation and coordination interactions, while its ionic character suspends phosphoryl cation exchange interactions. Some applications elute hydroxyapatite with combinations of phosphate and chloride salts. Chlorides preferentially elute the phosphoryl cation exchange interaction while having relatively little effect on calcium affinity interactions. (Gagnon et al, *Bioprocess International*, 4(2) 50 (2006)).

Native hydroxyapatite and fluorapatite can be converted to calcium-derivatized forms by exposure to soluble calcium in the absence of phosphate. (Gorbunoff, *Anal. Biochem.*, 136 425 (1984)). This converts P-sites into secondary C-sites, abolishing phosphoryl cation exchange interactions, increasing the number of C-sites, and fundamentally altering the selectivity of the apatite support. Small alkaline proteins typified by lysozyme (13.7-14.7 Kda, pI 10.7) and ribonuclease (14.7 kDa, pI 9.5-9.8) fail to bind to calcium-derivatized apatites, but most other proteins bind so strongly that even 3 M calcium chloride is inadequate to achieve elution (Gorbunoff). Other chloride salts also fail to achieve elution. Calcium-derivatized apatites are restored to their native forms by exposure to phosphate buffer, at which point they may be eluted by methods commonly applied for elution of native apatite supports.

The effects of different salts on the selectivity of a given apatite are unpredictable. For example, in the absence of phosphate, sodium chloride is unable to elute most IgG monoclonal antibodies from native hydroxyapatite, even at concentrations in excess of 4 moles per liter (Gagnon et al, 2006, *Bioprocess International*, 4(2) 50). This implies extremely strong binding. In exclusively phosphate gradients, IgG is typically one of the latest eluting proteins, usually requiring 100-150 mM phosphate. This also implies strong binding. When eluted with a combination of lower concentrations of both salts, such as 0.25 M sodium chloride and 50 mM phosphate however, IgG is one of the earliest eluting proteins. Other paradoxes reinforce the point: increasing the sodium chloride concentration in the presence of phosphate, which causes IgG to bind less strongly, has the opposite effect on DNA (Gagnon et al, 2005, *Bioprocess International*, 3(7) 52-55). Additionally, lysozyme elutes at a higher phosphate concentration than BSA in the absence of sodium chloride but fails to bind in the presence of 1 M sodium chloride.

Ammonium sulfate, sodium sulfate, and other sulfate salts are commonly used for precipitation of proteins, or to cause proteins to bind to hydrophobic interaction chromatography media. They can also be used to enhance binding with biological affinity chromatography media such as protein A, and have even been reported to cause proteins to bind to ion exchangers (Gagnon, 1996, *Purification Tools for Monoclonal Antibodies*, ISBN 0-9653515-9-9; Mevarech et al, 1976, *Biochemistry*, 15, 2383-2387; Leicht et al, 1981, *Anal. Biochem.*, 114, 186-192; Arakawa et al, 2007, *J. Biochem. Biophys. Met.*, 70, 493-498). Sulfates have occasionally been reported for elution of ion exchangers at low concentrations for research applications but are seldom exploited in preparative applications due to concerns over protein precipitation (Kopaciewicz et al, 1983, *J. Chromatogr.*, 266 3-21; Gooding et al, 1984, *J. Chromatogr.*, 296, 321-328; Rounds et al, 1984, *J. Chromatogr.*, 283 37-45). None of these methods is an appropriate model for apatites because none of them exploits calcium affinity for binding.

Several authors have concluded that, "The presence of . . . $(NH_4)_2SO_4$ seems not to affect the elution [of hydroxyapatite]." (Karlsson et al, 1989, in *Protein Purification: Principles, High Resolution Methods, and Applications*, Chapter 4, ISBN 0-89573-122-3). Even this reference mentions the application of sulfate strictly in the context of phosphate gradients. In the rare cases where alternatives to phosphate as a primary eluting salt have been discussed in the literature, suggestions have included calcium chloride, citrate and fluoride salts, but without mention of sulfates (Gagnon, 1996; Karlsson et al, 1989; Gorbunoff). Other publications indicate that sulfate salts in particular should be unsuitable as primary eluting agents for hydroxyapatite because " . . . $SO_3H$ do[es] not form complexes with calcium." (Gorbunoff).

Borate salts have been likewise overlooked. Borate is occasionally used in the field of chromatography as a buffering agent at pH values from about 8.8 to 9.8

(pK~9.24). It is also used infrequently at alkaline pH to modify the charge characteristics of cis-diol compounds to selectively enhance their retention on anion exchangers. In contrast to phosphates, chlorides, and sulfates, all of which exhibit molar conductivities of about 90 mS/cm, a 1 M solution of borate at pH 7 has a molar conductivity of about 9 mS.

Acetates have been compared to chlorides for hydroxyapatite separation of IgG from aggregates and were found to support inferior fractionation (Gagnon et al, Practical issues in the industrial use of hydroxyapatite for purification of monoclonal antibodies, Poster, 22$^{nd}$ national meeting of the American Chemical Society, San Francisco, Sep. 10-14, 2006 <http://www.validated.com/revalbio/pdffiles/ACS_CHT_02.pdf>. Monocarboxylic acid salts have been neglected, and the elution potential of monocarboxylic zwitterions totally so.

Hydroxyapatite is used for purification of antibodies and antibody fragments (Bowles et al, Int. J. Pharmacol., 10 537 (1988); Guerrier et al, J. Chromatography B, 755 37 (2001); Gagnon et al, BioProcess Int., 4(2) 50 (2006)). The column is usually equilibrated and the sample applied in a buffer that contains a low concentration of phosphate. Adsorbed antibodies are usually eluted in an increasing gradient of phosphate salts. Alternatively, they may be eluted in an increasing gradient of chloride salts but both elution formats impose disadvantages on purification procedures. The high phosphate concentration in which antibodies elute in phosphate gradients has strong buffer capacity that may interfere with subsequent purification steps. The high conductivity at which antibodies elute in chloride gradients may also interfere with downstream steps. Both situations require either that the eluted antibody be diluted extensively, or that it be buffer-exchanged, for example by diafiltration, in order to modify the conditions to render the antibody preparation suitable for application to a subsequent purification step. Dilution and buffer exchange have a negative impact on process economics. As a result, apatite chromatography steps are often placed at the end of a purification process. This tends to eliminate them from consideration as capture steps. It also discourages the use of HA as an intermediate step. A further disadvantage of chloride gradients is that the application of chloride to hydroxyapatite causes an uncontrolled reduction of pH. Acidic pH causes destruction of hydroxyapatite and risks adverse affects to antibodies bound to it.

Another limitation of hydroxyapatite with antibody purification is that IgG binding capacity is reduced at elevated conductivity values. This strongly reduces its versatility since the salt concentration of cell culture supernatants and antibody-containing fractions from purification methods such as ion exchange and hydrophobic interaction chromatography, confers sufficient conductivity to reduce the IgG binding capacity of hydroxyapatite to such an extent that it may not be useful for a particular application. This disadvantage can be overcome by diafiltration or dilution of the sample prior to its application to the hydroxyapatite column, but as noted above, these operations increase the expense of the overall purification process. Alternatively, the disadvantage can be ameliorated by using a larger volume of hydroxyapatite, but this increases process expense by requiring larger columns and larger buffer volumes. It also causes the antibody to elute in a larger volume of buffer, which increases overall process time in the subsequent purification step.

SUMMARY OF THE INVENTION

The present invention in certain embodiments relates to methods of fractionating or purifying a desired antibody or immunoreactive antibody fragment from an impure preparation by contacting said preparation with a native or calcium-derivatized apatite chromatography support, then eluting the support in the presence of an ionic species which is a sulfate, borate, monocarboxylic organic acid salt or monocarboxylic zwitterion. In certain embodiments the ionic species is the primary eluting ion in the eluent. In certain embodiments the eluent is substantially free of phosphate as an eluting ion.

In certain embodiments of the inventions, a method for purifying an antibody or antibody fragment from an impure preparation is provided wherein the impure preparation is contacted with an apatite chromatography support in either the calcium derivatized form or in its native form and the apatite support is converted to the other form prior to elution of the antibody or antibody fragment.

DETAILED DESCRIPTION OF THE INVENTION

Advantages of some embodiments of the invention include the following: 1) Calcium-derivatized apatites support higher binding capacity than native hydroxyapatite for most antibodies, even at high conductivity values, thereby making apatite chromatography more effective as a capture method, or as an intermediate fractionation step following high-salt elution from another fractionation step such as ion exchange or hydrophobic interaction chromatography; 2) Calcium-derivatized apatites also produce unique selectivities that may enable effective antibody or antibody fragment fractionation, including removal of aggregates, in situations where native apatites fail to do so; 3) Antibodies or fragments thereof may be bound to a native apatite support which is then converted to the calcium-derivatized form to achieve a particular selectivity for elution or; 4) Antibodies or fragments thereof may be bound to a calcium-derivatized apatite support which is them converted to the native form for elution. 5) Sulfate, borate, and certain monocarboxylic acids or zwitterions are able to elute antibodies from apatite supports in the absence of phosphate; 6) Elution in the presence of sulfate, borate, or monocarboxylic acids or zwitterions produces unique selectivities that permit effective fractionation of antibodies or antibody fragments, including removal of aggregates, that may not be adequately served by elution with phosphate or by combinations of phosphate and chloride; 7) Borate permits elution of antibodies and antibody fragments at low conductivity values, and does so without imposing significant buffer capacity at neutral pH, thereby facilitating use of the eluted antibody or antibody fragment in subsequent ion exchange chromatography steps without the necessity for intervening steps such as diafiltration; 8) Borate and certain monocarboxylic acids or zwitterions create an increase in pH on contact with apatites which can be used to counteract the effect of chlorides on pH, thereby attenuating or eliminating the pH reduction that otherwise accompanies the introduction of chlorides; 9) Sulfate enhances the separation of antibodies and antibody fragments from phosphorylated contaminants.

In certain embodiments the ionic species is borate. In certain embodiments the borate is sodium borate or potassium borate. In certain such embodiments the primary eluting ion is borate. In certain embodiments the borate is present at a pH where the borate lacks substantial buffering capacity; in certain such embodiments the pH is less than 8.7. In certain other embodiments the borate is present at greater than 50 mM and at a pH where the borate has substantial buffering capacity; in certain such embodiments the pH is 8.7 or greater.

In certain embodiments the ionic species is sulfate. In certain embodiments the sulfate is sodium or potassium sulfate. In certain embodiments the sulfate is the primary eluting ion.

In certain embodiments the ionic species is a monocarboxylic acid salt. In certain such embodiments the monocarboxylate acid anion is formate, acetate, lactate, succinate, pyruvate, gluconate, glucuronate or proprionate. In certain embodiments the monocarboxylate is the primary eluting ion.

In still other embodiments the ionic species is a monocarboxylic zwitterion. In certain such embodiments the monocarboxylate zwitterion is glycine, proline, lysine or histidine.

In some embodiments, the impure antibody or fragment preparation may be applied to the apatite chromatography support under conditions that permit the binding of protein contaminants, intact non-aggregated antibody, antibody fragments, and aggregated antibody, with purification being achieved subsequently by application of an elution gradient. This mode of chromatography is often referred to as bind-elute mode.

In some embodiments, the impure antibody or fragment preparation may be applied to the apatite chromatography support under conditions that prevent the binding of intact non-aggregated antibody or the desired antibody fragment while binding contaminants. This mode of application is often referred to as flow-though mode. Bound contaminants may be removed subsequently from the column by means of a cleaning step.

Suitable apatite chromatography supports include native hydroxyapatite, calcium-derivatized hydroxyapatite, native fluorapatite, and calcium-derivatized fluorapatite.

In certain embodiments, elution may be achieved exclusively by means of increasing the concentration of the ionic species such as borate, sulfate, or monocarboxylic acids or zwitterions. In certain of such embodiments such elution is achieved with a single ionic species as the eluting ion, e.g., borate or sulfate.

In some embodiments, elution may be achieved by borate in combination with calcium, magnesium, phosphate, sulfate, chloride, monocarboxylic acids or zwitterions, arginine, glycine, urea, or nonionic organic polymers.

In some embodiments, elution may be achieved by sulfate in combination with calcium, magnesium, phosphate, borate, chloride, monocarboxylic acids or zwitterions, arginine, glycine, urea, or nonionic organic polymers.

In some embodiments, elution may be achieved by monocarboxylic acids or zwitterions in combination with calcium, magnesium, phosphate, borate, sulfate, chloride, arginine, glycine, urea, or nonionic organic polymers.

In certain embodiments, the method for purifying an antibody or immunoreactive antibody fragment from an impure preparation containing said antibody or antibody fragment includes the steps of (a) contacting the impure preparation with an apatite chromatography support, wherein the apatite chromatography support is in a calcium-derivatized form when it is contacted with the antibody or antibody fragment and (b) substantially converting the calcium-derivatized apatite chromatography support to its native form prior to eluting the antibody or antibody fragment. In certain such embodiments the antibody or antibody fragment is eluted with phosphate as the primary eluting ion.

In certain embodiments, the method for purifying a non-aggregated antibody or immunoreactive antibody fragment from an impure preparation containing said antibody or antibody fragment involves the steps of (a) contacting the impure preparation with an apatite chromatography support, wherein the apatite chromatography support is in its native form when it is contacted with the antibody or antibody fragment and (b) substantially converting the native form apatite chromatography support to a calcium-derivatized form prior to eluting the antibody or antibody fragment. In certain such embodiments the conversion of the apatite chromatography support to the calcium derivatized form causes elution of the antibody or immunoreactive fragment of interest.

In certain embodiments, the antibody or antibody fragment is a mammalian immunoglobulin of the class IgA, IgD, IgE, IgG, or IgM of monoclonal or polyclonal origin, an avian immunoglobulin of the class IgY, or a fusion protein containing a portion of an antibody.

In certain embodiments, the antibody fragment is Fab, $F(ab')_2$, Fv, scFv, Fd, mAb, dAb or another fragmentary composition that retain antigen-binding function.

Embodiments of the invention may be practiced in combination with one or more other purification methods, including but not limited to size exclusion chromatography, protein A and other forms of affinity chromatography, anion exchange chromatography, cation exchange chromatography, hydrophobic interaction chromatography, mixed mode chromatography, and various filtration methods. It is within the ability of a person of ordinary skill in the art to develop appropriate conditions for these methods and integrate them with the invention herein to achieve purification of a particular antibody or antibody fragment.

Terms are defined so that the invention may be understood more readily. Additional definitions are set forth throughout this disclosure.

"Apatite chromatography support" refers to a mineral of calcium and phosphate in a physical form suitable for the performance of chromatography. Examples include but are not limited to hydroxyapatite and fluorapatite. This definition is understood to include both the native and calcium-derivatized forms of an apatite chromatography support.

"Salt" refers to an aqueous-soluble ionic compound formed by the combination of negatively charged anions and positively charged cations. The anion or cation may be of organic or inorganic origin. Anions of organic origin include but are not limited to acetate, lactate, malate, and succinate. Anions of inorganic origin include but are not limited to chloride, borate, sulfate, and phosphate. Cations of organic origin include but are not limited to arginine and lysine. Cations of inorganic origin include but are not limited to sodium, potassium, calcium, magnesium, and iron.

"Borate" refers to ionic compounds of boron and oxygen such as, but not limited to boric acid, sodium borate, and potassium borate.

"Phosphate" refers to salts based on phosphorus (V) oxoacids such as, but not limited to, sodium phosphate and potassium phosphate.

"Sulfate" refers to salts based on sulfur (VI) oxoacids such as, but not limited to sodium sulfate and ammonium sulfate.

"Chloride" refers to salts such as, but not limited to sodium chloride and potassium chloride.

"Monocarboxylic acid salt" or "Monocarboxylate" refers to organic acid salts having a single carboxylic acid moiety including but not limited to the sodium or potassium salts of formic, acetic, propionic, lactic, pyruvic, gluconic, or glucuronic acid.

"Monocarboxylic zwitterion" refers to a molecule containing a single carboxyl moiety and at least one moiety with a positive charge. Suitable examples include but are not limited to the amino acids glycine, proline, lysine, and histidine.

"Nonionic organic polymer" refers to any uncharged linear or branched polymer of organic composition. Examples include, but are not limited to, dextrans, starches, celluloses, polyvinylpyrrolidones, polypropylene glycols, and polyethylene glycols of various molecular weights. Polyethylene glycol has a structural formula HO—($CH_2$—$CH_2$—O)$_n$—H. Examples include, but are not limited to, compositions with an average polymer molecular weight ranging from 100 to 10,000 daltons. The average molecular weight of commercial PEG preparations is typically indicated by a hyphenated suffix. For example, PEG-600 refers to a preparation with an average molecular weight of about 600 daltons.

"Buffering compound" refers to a chemical compound employed for the purpose of stabilizing the pH of an aqueous solution within a specified range. Phosphate is one example of a buffering compound. Other common examples include but are not limited to compounds such as acetate, morpholinoethanesulfonic acid (MES), Tris-hydroxyaminomethane (Tris), and hydroxyethylpiperazinesulfonic acid (HEPES).

"Buffer" refers to an aqueous formulation comprising a buffering compound and other components required to establish a specified set of conditions to mediate control of a chromatography support. The term "equilibration buffer" refers to a buffer formulated to create the initial operating conditions for a chromatographic operation. "Wash buffer" refers to a buffer formulated to displace unbound contaminants from a chromatography support. "Elution buffer" refers to a buffer formulated to displace the one or more biomolecules from the chromatography support.

"Biomolecule" refers to a molecule of biological origin, composite, or fragmentary form thereof. Examples include but are not limited to proteins, polynucleotides, endotoxins, and viruses. Examples of proteins include but are not limited to antibodies, enzymes, growth regulators, clotting factors, and phosphoproteins. Examples of polynucleotides include DNA and RNA. Examples of viruses include enveloped and non-enveloped viruses.

"Antibody" refers to any immunoglobulin or composite form thereof. The term may include, but is not limited to polyclonal or monoclonal antibodies of the classes IgA, IgD, IgE, IgG, and IgM, derived from human or other mammalian cell lines, including natural or genetically modified forms such as humanized, human, single-chain, chimeric, synthetic, recombinant, hybrid, mutated, grafted, and in vitro generated antibodies. "Antibodies" may also include composite forms including but not limited to fusion proteins containing an immunoglobulin moiety.

"Antibody fragment" refers to any antibody fragment such as Fab, F(ab')$_2$, Fv, scFv, Fd, mAb, dAb or other compositions that retain antigen-binding function. Antibody fragments may be derived from human or other mammalian cell lines, including natural or genetically modified forms such as humanized, human, chimeric, synthetic, recombinant, hybrid, mutated, grafted, and in vitro generated, from sources including but not limited to bacterial cell lines, insect cell lines, plant cell lines, yeast cell lines, or cell lines of other origin. Antibody fragments may also be derived by controlled lysis of purified antibody with enzymes such as, but not limited to ficin, papain, or pepsin.

"Antibody aggregate" refers to an association of at least two antibodies. The association may be either covalent or non-covalent without respect to the mechanism by which the antibodies are associated. The association may be direct between the antibodies or indirect through other molecules that link the antibodies together. Examples of the latter include but are not limited to disulfide linkages with other proteins, hydrophobic associations with lipids, charge associations with DNA, affinity associations with leached protein A, or mixed mode associations with multiple components.

"Non-antibody proteins" refers to proteins formulated into antibody production media and/or to proteins produced by the cell line or host during antibody production.

"Antibody preparation" refers to any composition containing an intact non-aggregated antibody. Said preparation may contain antibody fragments and/or aggregates. Non-antibody proteins and other contaminants, potentially including but not limited to nucleic acids, endotoxin, and virus may also be present. An impure preparation from which an antibody is to be purified according to the invention can be an antibody preparation.

"Antibody fragment preparation" refers to any composition containing an immunoreactive antibody fragment. Said preparation may contain intact antibodies and/or aggregates. Non-antibody proteins and other contaminants, potentially including but not limited to host cell proteins, nucleic acids, endotoxin, and virus may also be present. An impure preparation from which an antibody fragment is to be purified according to the invention can be an antibody preparation.

As it relates to the invention herein, the term "bind-elute mode" refers to an operational approach to chromatography in which the buffer conditions are established so that the intact non-aggregated antibody or antibody fragment, and contaminants, bind to the column upon application, with fractionation being achieved subsequently by modification of the buffer conditions.

As it relates to the invention herein, the term "flow-through mode" refers to an operational approach to chromatography in which the buffer conditions are established so that the intact non-aggregated antibody or antibody fragment flows through the column upon application while contaminants are selectively retained, thus achieving their removal.

"Preparative applications" refers to situations in which the invention is practiced for the purpose of purifying intact non-aggregated antibody for research, diagnostic, or therapeutic applications. Such applications may be practiced at any scale, ranging from milligrams to kilograms of antibody per batch.

Materials

1. Apatite Chromatography Support

Various apatite chromatography supports are available commercially, any of which can be used in the practice of this invention. These include but are not limited to hydroxyapatite and fluorapatite. "Ceramic" hydroxyapatite (CHT™) or "ceramic" fluorapatite (CFT™) refer to forms of the respective minerals in which nanocrystals are aggregated into particles and fused at high temperature to create stable ceramic microspheres suitable for chromatography applications. Commercial examples of ceramic hydroxyapatite include, but are not limited to CHT Type I and CHT Type II. Commercial examples of fluorapatite include, but are not limited to CFT Type II. Unless specified, CHT and CFT refer to roughly spherical particles of any diameter, including but not limited to 10, 20, 40, and 80 micron. HA Ultrogel™ refers to a product comprising microfragments of non-ceramic hydroxyapatite embedded in porous agarose microspheres.

The choice of hydroxyapatite or fluorapatite, the type, and average particle diameter suitable for a particular application can be determined through experimentation by the skilled artisan.

The invention may be practiced in a packed bed column, a fluidized/expanded bed column containing the hydroxyapatite or fluorapatite, and/or a batch operation where the hydroxyapatite or fluorapatite is mixed with the solution for a certain time.

Certain embodiments employ CHT or CFT packed in a column.

Certain embodiments employ CHT or CFT, packed in a column of about 5 mm internal diameter and a height of about 50 mm, for evaluating the effects of various buffer conditions on the binding and elution characteristics of a particular antibody preparation of antibody fragment preparation.

Certain embodiments employ CHT or CFT, packed in columns of any dimensions required to support preparative applications. Column diameter may range from 1 cm to more than 1 meter, and column height may range from 5 cm to more than 30 cm depending on the requirements of a particular application.

Appropriate column dimensions can be determined by the skilled artisan.

2. Antibodies

Antibody preparations to which the invention can be applied may include unpurified or partially purified antibodies from natural, synthetic, or recombinant sources. Unpurified antibody preparations may come from various sources including, but not limited to, plasma, serum, ascites fluid, milk, plant extracts, bacterial lysates, yeast lysates, or conditioned cell culture media. Partially purified preparations may come from unpurified preparations that have been processed by at least one chromatography, precipitation, other fractionation step, or any combination of the foregoing. The chromatography step or steps may employ any method, including but not limited to size exclusion, affinity, anion exchange, cation exchange, protein A affinity, hydrophobic interaction, immobilized metal affinity chromatography, or mixed-mode chromatography. The precipitation step or steps may include salt or PEG precipitation, or precipitation with organic acids, organic bases, or other agents. Other fractionation steps may include but are not limited to crystallization, liquid:liquid partitioning, or membrane filtration.

3. Antibody Fragments

Antibody fragment preparations to which the invention can be applied may include unpurified or partially purified antibody fragments from natural, synthetic, or recombinant sources. Unpurified fragment preparations may come from various sources including, but not limited to, plasma, serum, ascites fluid, milk, plant extracts, bacterial lysates, yeast lysates, or conditioned cell culture media. Antibody fragment preparations may also include enzymatic digests of purified or partially purified antibodies, such as but not limited to IgG monoclonal antibodies digested with plasmin, ficin, or pepsin. Partially purified preparations may come from unpurified preparations that have been processed by at least one chromatography, precipitation, other fractionation step, or any combination of the foregoing. The chromatography step or steps may employ any method, including but not limited to size exclusion, affinity, anion exchange, cation exchange, protein A affinity, hydrophobic interaction, immobilized metal affinity chromatography, or mixed-mode chromatography. The precipitation step or steps may include salt or PEG precipitation, or precipitation with organic acids, organic bases, or other agents. Other fractionation steps may include but are not limited to crystallization, liquid:liquid partitioning, or membrane filtration.

B. DESCRIPTION OF THE METHOD

In preparation for contacting the antibody preparation or antibody fragment preparation with the hydroxyapatite or fluorapatite column, it is usually necessary to equilibrate the chemical environment inside the column. This is accomplished by flowing an equilibration buffer through the column to establish the appropriate pH, conductivity, concentration of salts; and/or the identity, molecular weight, and concentration of nonionic organic polymer.

The equilibration buffer for applications conducted in bind-elute mode may include phosphate salts at a concentration of about 5-50 mM, or calcium salts at a concentration of about 2-5 mM, but not mixtures of phosphate and calcium. It may optionally include a nonionic organic polymer at a concentration of about 0.01-50%, and a buffering compound to confer adequate pH control. Buffering compounds may include but are not limited to MES, HEPES, BICINE, imidazole, and Tris. The pH of the equilibration buffer for hydroxyapatite may range from about pH 6.5 to pH 9.0. The pH of the equilibration buffer for fluorapatite may range from about pH 5.0 to 9.0.

In one embodiment, the equilibration buffer contains sodium phosphate at a concentration of about 5 mM at a pH of 6.7, in the presence or absence of MES or Hepes at a concentration of about 20-50 mM.

In one embodiment, the equilibration buffer contains a calcium salt at a concentration of about 2.5 mM, in the presence of Hepes at a concentration of about 20-50 mM and a pH of about 7.0.

The antibody preparation or antibody fragment preparation may also be equilibrated to conditions compatible with the column equilibration buffer before the invention is practiced. This consists of adjusting the pH, concentration of salts, and other compounds.

After the column and antibody preparation or antibody fragment preparation have been equilibrated, the antibody preparation may be contacted with the column. Said preparation may be applied at a linear flow velocity in the range of, but not limited to, about 50-600 cm/hr. Appropriate flow velocity can be determined by the skilled artisan.

In one embodiment of the bind-elute mode, a column equilibrated in phosphate to obtain a particular binding selectivity during column loading may be switched to calcium to obtain a particular elution selectivity. Or the opposite may be performed, with a column equilibrated to calcium to obtain a particular binding selectivity, and then switched to phosphate to obtain a particular elution selectivity.

In one embodiment of the flow-through mode, non-aggregated antibody flows through the column and is collected, while aggregated antibody binds to the column. The antibody preparation is followed with a wash buffer, usually of the same composition as the equilibration buffer. This displaces remaining non-aggregated antibody from the column so that it can be collected. Retained aggregates may optionally be removed from the column with a cleaning buffer of about 500 mM sodium phosphate, among others.

In one embodiment of the flow-through mode, the desired antibody fragment flows through the column and is collected, while contaminants bind to the column. The fragment preparation is followed with a wash buffer, usually of the same composition as the equilibration buffer. This displaces remaining fragment from the column so that it can be collected. Retained contaminants may optionally be removed from the column with a cleaning buffer of about 500 mM sodium phosphate, among others.

In one embodiment of an application conducted in bind-elute mode, some combination of unwanted antibody fragments, intact non-aggregated antibody, and aggregated antibody bind to the column. The antibody preparation is followed with a wash buffer, usually of the same composition as the equilibration buffer. This removes unretained contaminants from the column. Unwanted antibody fragments may be selectively displaced by a wash buffer that removes fragments without removing intact non-aggregated antibody. Intact non-aggregated antibody is then eluted from the column under conditions that leave aggregated antibody bound to the column. Retained aggregates may optionally be removed from the column with a cleaning buffer of about 500 mM sodium phosphate, among others.

In one embodiment of an application conducted in bind-elute mode, the desired antibody fragment and contaminants bind to the column. The antibody fragment preparation is followed with a wash buffer, usually of the same composition as the equilibration buffer. This removes unretained contaminants from the column. The desired antibody fragment is then eluted from the column under conditions that leave contaminants bound to the column. Retained contaminants may optionally be removed from the column with a cleaning buffer.

In one embodiment of the bind-elute mode, the wash buffer may have a formulation different than the equilibration buffer.

After use, the apatite column may optionally be cleaned, sanitized, and stored in an appropriate agent.

The invention may be practiced in combination with other purification methods to achieve the desired level of antibody or fragment purity. The invention may be practiced at any point in a sequence of 2 or more purification methods.

It will be apparent to the person of ordinary skill that the invention will have a beneficial effect on removal of other contaminants, such as nucleic acids, endotoxin, virus, and complexes of antibody with leached protein A.

C. EXAMPLES

Considerable variation in chromatographic behavior is encountered from one antibody or fragment preparation to another. This includes variation in the composition and proportion of non-antibody proteins, intact antibody, antibody fragments, and antibody aggregates that contaminate various preparations, as well as variation in the individual retention characteristics of different constituents. This makes it necessary to customize the buffer conditions to apply the invention to its best advantage in each situation. This may involve adjustment of pH, the concentration salts, the concentration of buffering components, and the content of nonionic organic polymer. Appropriate levels for the various parameters and components can be determined systematically by a variety of approaches. The following examples are offered for illustrative purposes only.

Example 1. Dynamic Binding Capacity Comparison of Native and Calcium-Derivatized Hydroxyapatite A column of hydroxyapatite, CHT Type II, 40 micron, 5 mm diameter, 50 mm height, was equilibrated at a linear flow rate of 300 cm/hr with 20 mM Hepes, 3 mM $CaCl_2$, pH 6.7. A sample of protein A purified IgG monoclonal antibody was applied to the column by in-line dilution at a proportion of 1 part antibody to 4 parts equilibration buffer. Dynamic breakthrough capacity at 5% breakthrough was 114 mg/mL of hydroxyapatite. The experiment was repeated with an equilibration buffer of 20 mM Hepes, 3 mM $CaCl_2$, 1 M NaCl, pH 6.7. Dynamic capacity at 5% breakthrough was 43 mg/mL. The experiment was repeated with an equilibration buffer of 5 mM sodium phosphate, pH 6.7. Dynamic capacity at 5% breakthrough was 29 mg/mL. The experiment was repeated with an equilibration buffer of 5 mM sodium phosphate, 1 M NaCl, pH 6.7. Dynamic capacity at 5% breakthrough was 3 mg/mL. This example illustrates the dramatic improvement in antibody binding capacity that is achieved by calcium derivatized apatite. It will be recognized by the skilled practitioner that a similar benefit may be obtained by substituting magnesium for calcium.

Example 2. Purification of an IgG Monoclonal Antibody from Cell Culture Supernatant on Native Hydroxyapatite, Eluted with a Borate Gradient A column of hydroxyapatite, CHT Type I, 40 micron, 8 mm diameter, 50 mm height, was equilibrated at a linear flow rate of 300 cm/hr with 5 mM sodium phosphate, 20 mM Hepes, pH 7.0. A monoclonal antibody preparation consisting of a mammalian cell culture supernatant previously filtered through a membrane with porosity of about 0.22 μm, and diafiltered to about the same conditions as the equilibration buffer was applied to the column. The column was eluted with a linear gradient to 1 M sodium borate, 5 mM sodium phosphate, pH 7.0. The majority of contaminating proteins eluted before the antibody. Non-aggregated antibody eluted at an average conductivity of about 5 mS/cm. Aggregates eluted later. The column was cleaned with 500 mM sodium phosphate, pH 7.0. It will be recognized by the person of ordinary skill in the art that eluted antibody may be further purified by additional purification methods, and that the low conductivity and buffer capacity of the eluted antibody fraction will facilitate such methods.

Example 3. Purification of an IgG Monoclonal Antibody from Cell Culture Supernatant on Native Hydroxyapatite, Eluted with a Monocarboxylic Acid (Lactate) Gradient A column of hydroxyapatite, CHT Type I, 40 micron, 5 mm diameter, 50 mm height, was equilibrated at a linear flow rate of 600 cm/hr with 5 mM sodium phosphate, 20 mM Hepes, pH 7.0. 100 microliters of a monoclonal antibody preparation consisting of a mammalian cell culture supernatant previously filtered through a membrane with porosity of about 0.22 μm, was injected onto the column and the column washed with 2 column volumes of equilibration buffer. The column was eluted with a 20 column volume linear gradient to 1 M sodium lactate, 20 mM Hepes, pH 7.0. The majority of contaminating proteins eluted before the antibody and most of the remainder eluted later. Non-aggregated antibody eluted at an average conductivity of about 20 mS/cm. Aggregates eluted later. The column was cleaned with 500 mM sodium phosphate, pH 7.0.

Example 4. Purification of an IgG Monoclonal Antibody from Cell Culture Supernatant on Native Hydroxyapatite, Eluted with a Borate Gradient The same column was prepared with the same buffers but with a different IgG monoclonal antibody. The majority of contaminating proteins eluted as previously but the antibody eluted only partially within the gradient. The run was repeated but with 20 mM phosphate in the equilibration and elution buffers. Under these conditions, the antibody eluted completely within the gradient. Antibody aggregate eluted after non-aggregated antibody. This example illustrates one way to adapt the procedure to antibodies that may not elute fully within the gradient. The phosphate concentration may be increased more if necessary. Alternatively or additionally, the borate concentration and/or pH of the eluting buffer may be increased.

Example 5. Purification of an IgG Monoclonal Antibody from Cell Culture Supernatant on Calcium Derivatized Hydroxyapatite, Eluted with a Borate Gradient A column of hydroxyapatite, CHT Type I, 40 micron, 8 mm diameter, 50 mm height, was equilibrated at a linear flow rate of 300 cm/hr with 2.5 mM calcium chloride, 20 mM Hepes, pH 7.0. A monoclonal antibody preparation consisting of cell culture supernatant previously filtered through a membrane with porosity of about 0.22 µm and diafiltered to about the same conditions as the equilibration buffer was applied to the column. The column was eluted with a linear gradient to 1 M sodium borate, 2.5 mM calcium chloride, 10% PEG-600, pH 7.0. The majority of contaminating proteins eluted before the antibody. Antibody aggregate eluted after non-aggregated antibody. The column was cleaned with 500 mM sodium phosphate, pH 7.0. PEG is known to have the general effect of enhancing the separation between fragments, intact antibody, and aggregates on hydroxyapatite. The skilled practitioner will recognize how to adjust the PEG concentration to optimize the results.

Example 6. Monoclonal Antibody Capture on Calcium-Derivatized Hydroxyapatite and Elution in a Sulfate Gradient A column of hydroxyapatite, CHT Type II, 40 micron, 5 mm diameter, 50 mm height, was equilibrated at a linear flow rate of 300 cm/hr with 20 mM Hepes, 3 mM $CaCl_2$, pH 6.7. Cell culture supernatant containing approximately 60 mg monoclonal IgG was equilibrated to 5 mM calcium by addition of 1 M calcium chloride at a proportion of 0.5%, then filtered to 0.22 microns. The sample was applied to the column. No antibody was detected in the flow-through. The column was washed with equilibration buffer, then eluted with a 20 column volume (CV) linear gradient to 20 mM Hepes, 3 mM $CaCl_2$, 0.5 M sodium sulfate, pH 6.7. The antibody eluted in a single peak at about 0.25 M sodium sulfate.

Example 7. Monoclonal Antibody Capture on Calcium-Derivatized Hydroxyapatite, Conversion to Native Hydroxyapatite, and Elution in a Phosphate Gradient A column of hydroxyapatite, CHT Type II, 40 micron, 5 mm diameter, 50 mm height, was equilibrated at a linear flow rate of 300 cm/hr with 20 mM Hepes, 3 mM $CaCl_2$, pH 6.7. Cell culture supernatant containing monoclonal approximately 40 mg IgG was equilibrated to 5 mM calcium by addition of 1 M calcium chloride at a proportion of 0.5%, then filtered to 0.22 microns. The sample was applied to the column. No antibody was detected in the flow-through. The column was washed with 5 mM sodium phosphate, 20 mM MES, pH 6.7, then eluted with a 20 CV linear gradient to 300 mM phosphate, pH 6.7. The antibody eluted in a single peak at about 165 mM sodium phosphate. This example illustrates the use of calcium-derivatized hydroxyapatite to obtain high binding capacity, followed by conversion to and elution from native hydroxyapatite.

Example 8. Intermediate Purification of a Monoclonal Antibody by Binding in the Presence of Calcium, Conversion to Native Apatite, and Elution in a Sodium Chloride Gradient A column of hydroxyapatite, CHT Type II, 40 micron, 5 mm diameter, 50 mm height, was equilibrated at a linear flow rate of 300 cm/hr with 20 mM Hepes, 3 mM $CaCl_2$, pH 6.7. Approximately 50 mg of protein A purified monoclonal IgG was equilibrated to 5 mM calcium by addition of 1 M calcium chloride at a proportion of 0.5%, then filtered to 0.22 microns. The sample was applied to the column. No antibody was detected in the flow-through. The column was washed with 20 mM Hepes, 10 mM sodium phosphate, pH 6.7, then eluted with a 20 CV linear gradient to 20 mM Hepes, 10 mM phosphate, 1 M sodium chloride, pH 6.7. The antibody eluted in a single peak at 0.6 M sodium chloride, followed by a well-separated aggregate peak.

Example 9. Unwanted Fragment and Aggregate Removal from a Partially Purified IgG Monoclonal Antibody, on Native Hydroxyapatite, Eluted with a Borate Gradient A column of hydroxyapatite, CHT Type I, 40 micron, 8 mm diameter, 50 mm height, was equilibrated at a linear flow rate of 300 cm/hr with 5 mM sodium phosphate, 20 mM Hepes, pH 7.0. A monoclonal antibody preparation previously purified by protein A affinity chromatography was applied to the column. The column was eluted with a linear gradient to 1 M sodium borate, 5 mM sodium phosphate, 20 mM Hepes, pH 7.0. The majority of fragments eluted before the antibody. Antibody aggregates and other contaminating proteins eluted after non-aggregated antibody. The column was cleaned with 500 mM sodium phosphate, pH 7.0.

Example 10. Bind-Elute Mode, Comparison of Monoclonal IgM Elution in Phosphate and Sulfate Gradients A column of hydroxyapatite, CHT Type II, 40 micron, 5 mm diameter, 50 mm height, was equilibrated at a linear flow rate of 200 cm/hr with 20 mM Hepes, 3 mM $CaCl_2$, pH 6.7. Cell supernatant containing a monoclonal IgM antibody was applied to the column. The column was eluted with a 20 CV linear gradient to 20 mM Hepes, 3 mM $CaCl_2$, 1.0 M sodium sulfate, pH 6.7. The center of the IgM peak eluted about 415 mM sodium sulfate. DNA eluted at 855 mM sulfate under these conditions. IgM aggregates did not elute within the sulfate gradient and were removed in a subsequent wash step with 500 mM phosphate. The experiment was repeated except that the column was equilibrated with 10 mM sodium phosphate pH 6.7 and eluted with a 20 CV linear gradient to 500 mM sodium phosphate, pH 6.7. The center of the IgM peak eluted at about 207 mM phosphate, essentially co-eluting with DNA as revealed by its elution at 205 mM phosphate. IgM aggregates were only partially eliminated. This example again illustrates the dramatic difference of selectivity between sulfate and phosphate gradients, specifically and dramatically highlights how sulfate gradients are more effective for removal of DNA from IgM preparations, and specifically illustrates the superior ability of sulfate gradients to eliminate aggregates.

Example 11. Purification of Fab

A column of hydroxyapatite, CHT Type I, 40 micron, 8 mm diameter, 50 mm height, was equilibrated at a linear flow rate of 300 cm/hr with 5 mM sodium phosphate, 20 mM Hepes, pH 7.0. A Fab preparation from papain digestion of an IgG monoclonal antibody was applied to the column. The column was eluted with a linear gradient to 1 M sodium borate, 5 mM sodium phosphate, 20 mM Hepes, pH 7.0. The majority of contaminating Fc fragments eluted before the Fab. Intact antibody eluted after the Fab. The column was cleaned with 500 mM sodium phosphate, pH 7.0.

Example 12. Purification of F(ab')$_2$

A column of hydroxyapatite, CHT Type I, 40 micron, 8 mm diameter, 50 mm height, was equilibrated at a linear flow rate of 300 cm/hr with 5 mM sodium phosphate, 20 mM Hepes, pH 7.0. A F(ab')$_2$ preparation from pepsin digestion of an IgG monoclonal antibody was applied to the column. The preparation contained no intact IgG. The column was eluted with a linear gradient to 1 M boric acid, 5 mM sodium phosphate, pH 7.0. The majority of contaminating Fc fragments eluted before the F(ab')$_2$. The column was cleaned with 500 mM sodium phosphate, pH 7.0.

Example 13. Purification of F(ab')$_2$

A column of hydroxyapatite, CHT Type I, 40 micron, 8 mm diameter, 50 mm height, was equilibrated at a linear flow rate of 300 cm/hr with 2.5 mM calcium chloride, 20 mM Hepes, pH 7.0. A F(ab')$_2$ preparation from pepsin digestion of an IgG monoclonal antibody was applied to the column. The column was eluted with a linear gradient to 1 M boric acid, 2.5 mM calcium chloride, 20 mM Hepes, pH 7.0. The majority of contaminating Fc fragments eluted before the F(ab')$_2$. The preparation contained no intact IgG. The column was cleaned with 500 mM sodium phosphate, pH 7.0.

Example 14. 2-Step Fab Purification on Calcium-Derivatized Hydroxyapatite and Cation Exchange Chromatography A column of hydroxyapatite, CHT Type I, 20 micron, 5 mm diameter, 50 mm height, was equilibrated with 10 mM sodium Hepes, 2.5 mM calcium chloride, pH 7.0 at a linear flow rate of 300 cm/hr. Calcium chloride was added to a Fab digest to a final concentration of 2.5 mM, then loaded onto the column. The Fab was unretained and flowed through the column at a purity of about 95%. The pH of the Fab fraction was titrated to pH 5.5 by addition of 1 M MES, pH 5.5, and applied to a cation exchange column (BIA Separations, CIM S) equilibrated to 20 mM MES, pH 5.5. The Fab bound and was eluted in a gradient of increasing pH, yielding a Fab fraction of purity greater than 99%. This example illustrates 2 important points: 1) the unique selectivity of calcium derivatized apatite, and 2) its ability in this case to elute the product at low conductivity and buffer capacity so as to facilitate a subsequent cation exchange chromatography step. It will be apparent to the skilled practitioner that the order of steps could be reversed to achieve a similar result, and that an additional step or steps could be added to achieve clinical purity.

Example 15. 2-Step Fab Purification on Calcium-Derivatized Hydroxyapatite and Hydrophobic Interaction Chromatography A column of hydroxyapatite, CHT Type I, 20 micron, 5 mm diameter, 50 mm height, was equilibrated with 10 mM sodium Hepes, 2.5 mM calcium chloride, 1 M sodium chloride, pH 7.0 at a linear flow rate of 300 cm/hr. A Fab preparation was titrated to 2 M sodium chloride, 2.5 mM calcium chloride, pH 7.0, then loaded onto the hydroxyapatite column. The Fab was unretained and flowed through the column at a purity of about 95%. The Fab fraction was diluted 1:1 with 4 M sodium chloride, 20 mM Hepes, pH 7.0, then loaded onto a hydrophobic interaction column (Tosoh Phenyl 600M) equilibrated to 2 M sodium chloride, 5 mM EDTA, 20 mM Hepes, pH 7.0. The Fab bound and was eluted in a gradient of decreasing salt concentration, yielding a Fab fraction of purity greater than 99%. The experiment was repeated, with the original Fab preparation diluted in 9 parts spent mammalian cell culture supernatant. The results were essentially the same, demonstrating that the majority of host cell proteins, as well as Fc-containing proteins, bound to the calcium derivatized hydroxyapatite. These experiments illustrate several important points: 1) the demonstrate another aspect of the unique selectivity of calcium-derivatized apatite, in this case illustrating its ability to bind contaminants even at high conductivity, 2) how the sample application conditions facilitate application of the HA-eluted Fab to a hydrophobic interaction chromatography column, and 3) that the method works equally well with simple preparations, such as enzyme digests, or with complex preparations, such as cell culture supernatants. It will be apparent to the skilled practitioner that the order of steps could be reversed to achieve a similar result, and that an additional step or steps could be added to achieve clinical purity.

Example 16. 2-Step Fab Elution from Native Hydroxyapatite by Conversion to Calcium Derivatized Hydroxyapatite, and Cation Exchange Chromatography A column of hydroxyapatite, CHT Type I, 20 micron, 5 mm diameter, 50 mm height, was equilibrated with 5 mM sodium phosphate, 10 mM Hepes, pH 7.0 at a linear flow rate of 300 cm/hr. A Fab preparation was titrated to 5 mM phosphate and loaded onto the hydroxyapatite column. The Fab was retained and eluted with a step to 10 mM Hepes, 2.5 mM calcium chloride, pH 7.0. Purity was greater than 95%. The pH of the Fab fraction was titrated to pH 5.5 by addition of 1 M MES, pH 5.5, and applied to a cation exchange column (BIA Separations, CIM S) equilibrated to 20 mM MES, pH 5.5. The Fab bound. The column washed with 10 mM MES, 2.5 mM EDTA, pH 5.5, then eluted in a linear pH gradient to 10 mM Hepes, pH 7.5, yielding a Fab fraction of purity greater than 99%. This example illustrates an important benefit of switching from native hydroxyapatite for sample loading to calcium-derivatized apatite for elution: The ability of Fab to bind native apatite under these conditions provides a means to concentrate the product from a dilute feed stream. The skilled practitioner will recognize that the cation exchange step could optionally have been eluted with a gradient of increasing conductivity, or a combination of pH and conductivity.

Example 17. 1-Step Purification of F(ab')$_2$ on Native Hydroxyapatite with an Increasing Sodium Chloride Gradient F(ab')$_2$ was prepared from purified IgG by enzymatic digestion with pepsin. It was applied to a column of native hydroxyapatite in 5 mM sodium phosphate and eluted with a gradient to 5 mM phosphate, 500 mM sodium chloride, pH 7. F(ab')$_2$ eluted at about 250 mM sodium chloride. Most of the Fc contamination eluted after the F(ab')$_2$ peak, but some co-eluted with the product. This contamination was mostly avoided in subsequent experiments by performing a wash, after sample injection, of 25 mM sodium phosphate, pH 7.0. After the wash, the column was re-equilibrated to 5 mM phosphate and eluted with a sodium chloride gradient as described above. The column was subsequently cleaned with 500 mM phosphate, pH 7.0.

Example 18. 1-Step Purification of F(ab')$_2$ on Native Hydroxyapatite with an Increasing Sodium Borate Gradient F(ab')$_2$ was prepared from purified IgG by enzymatic digestion with pepsin. It was applied to a column of native hydroxyapatite in 5 mM sodium phosphate, 20 mM Hepes, pH 7.0, and eluted with a gradient to 5 mM phosphate, 500 mM sodium borate, pH 7. Most of the Fc contamination eluted after the F(ab')$_2$ peak but some co-eluted. This contamination was mostly avoided in subsequent experiments by performing a wash, after sample injection, of 25 mM sodium phosphate, pH 7.0. After the wash, the column was re-equilibrated to 5 mM phosphate and eluted with a sodium chloride gradient as described above. It will be recognized by the skilled practitioner that the low conductivity and buffering capacity of the borate-eluted F(ab')$_2$ make it better suited for subsequent purification by cation exchange chromatography than elution in a sodium chloride gradient. It will be equally recognized that the substitution of borate with monocarboxylic acids or zwitterions with molar conductivities lower than sodium chloride may confer a similar benefit.

Example 198. Purification of F(ab')$_2$ on Calcium Derivatized Hydroxyapatite with an Increasing Ammonium Sulfate Gradient F(ab')$_2$ was prepared from purified IgG by enzymatic digestion with pepsin. It was applied to a column of calcium derivatized hydroxyapatite in 2.5 mM calcium chloride, 20 mM Hepes, pH 7.0. A small amount of non-F(ab')$_2$ proteins were unretained and flowed through the column. The column was washed with equilibration buffer, then eluted with a linear gradient to 1.0 M ammonium sulfate, 2.5 mM calcium chloride, 20 M Hepes, pH 7.0. The skilled practitioner will recognize that elution in ammonium sulfate facilitates application of the F(ab')$_2$ fraction to a hydrophobic interaction column for additional purification.

Example 20. Bind-Elute Mode, Comparison of DNA Elution in Phosphate and Sulfate Gradients A column of hydroxyapatite, CHT Type II, 40 micron, 5 mm diameter, 50 mm height, was equilibrated at a linear flow rate of 300 cm/hr with 20 mM Hepes, 3 mM CaCl$_2$, pH 6.7. A sample of DNA isolated from salmon sperm was applied to the column. The column was eluted with a 20 CV linear gradient to 20 mM Hepes, 3 mM CaCl$_2$, 1.0 M sodium sulfate, pH 6.7. The center of the DNA peak eluted at about 855 mM sodium sulfate. The experiment was repeated except that the column was equilibrated with 10 mM sodium phosphate pH 6.7 and eluted with a 20 CV linear gradient to 500 mM sodium phosphate, pH 6.7. The center of the DNA peak eluted at about 205 mM sodium phosphate. This example illustrates the dramatic difference between selectivity of sulfate and phosphate gradients. It will be apparent to the skilled practitioner that these results also show the ability of sulfate gradients to achieve more effective removal of DNA than phosphate gradients.

Example 21. Bind-Elute Mode, Comparison of Endotoxin Elution in Phosphate and Sulfate Gradients A column of hydroxyapatite, CHT Type II, 40 micron, 5 mm diameter, 50 mm height, was equilibrated at a linear flow rate of 300 cm/hr with 20 mM Hepes, 3 mM CaCl$_2$, pH 6.7. A sample of endotoxin prepared by phenol extraction from *Salmonella enterica* serotype *typhimurium* was applied to the column. The column was eluted with a 20 column volume (CV) linear gradient to 20 mM Hepes, 3 mM CaCl$_2$, 1.0 M sodium sulfate, pH 6.7. A minor fraction of endotoxin eluted early in the gradient, followed by a DNA contaminant peak at 855 mM sodium sulfate. The majority of the endotoxin failed to elute and was removed from the column by cleaning it with 500 mM sodium phosphate, pH 6.7. The experiment was repeated except that the column was equilibrated with 10 mM sodium phosphate pH 6.7 and eluted with a 20 CV linear gradient to 500 mM sodium phosphate, pH 6.7. A minor fraction of the endotoxin, corresponding to the early eluting population in the sulfate gradient, failed to bind in phosphate and flowed through the column immediately upon application. The center of the primary endotoxin peak eluted at 85 mM sodium phosphate. This example illustrates the dramatic difference between selectivity of sulfate and phosphate gradients in general, specifically illustrates the ability of sulfate gradients to achieve unique separations among differentially phosphorylated biomolecules, and specifically illustrates that some phosphorylated biomolecules do not elute from at least some apatite chromatography supports in sulfate gradients conducted in the absence of phosphate. It will be apparent to the skilled practitioner that these results also show the ability of sulfate gradients to achieve more effective removal of endotoxin than phosphate gradients.

Example 22. Improved pH Control by the Application of Borate

A column of hydroxyapatite was equilibrated to 5 mM sodium phosphate, pH 7.0. A gradient step of 0.5 M sodium chloride, 5 mM sodium phosphate, pH 7.0 was applied to the column. This caused the pH to drop to about pH 5.9. The column was re-equilibrated to 5 mM phosphate pH 7.0. A gradient step of 0.5 mM sodium chloride, 5 mM sodium phosphate, 50 mM sodium borate, pH 7.0 was applied to the column. Column pH dropped only to pH 6.7. It will be understood by the skilled practitioner that the same approach can be used to control pH in any situation where the introduction of an eluting agent causes an unacceptable reduction of pH, and that the borate concentration can be adjusted to achieve the desired degree of pH control. Like borate, the application of lactate to an equilibrated apatite support causes an increase in pH, which can likewise be exploited to manage uncontrolled pH reduction caused by chlorides. The skilled practitioner will recognize that other monocarboxylic acids or zwitterions may be substituted to produce a similar effect.

It will be understood by the person of ordinary skill in the art how to optimize and scale up the results from experiments such as those described in the above examples. It will also be understood by such persons that other approaches to method development, such as but not limited to high-throughput robotic systems, can be employed to determine the conditions that most effectively embody the invention for a particular antibody.

D. ADDITIONAL OPTIONAL STEPS

The present invention may be combined with other purification methods to achieve higher levels of purification, if necessary. Examples include, but are not limited to, other methods commonly used for purification of antibodies, such as size exclusion chromatography, protein A and other forms of affinity chromatography, anion exchange chromatography, cation exchange chromatography, hydrophobic interaction chromatography, immobilized metal affinity chromatography, mixed mode chromatography, precipitation, crystallization, liquid:liquid partitioning, and various filtration methods. It is within the purview of one of ordinary skill in the art to develop appropriate conditions for the various methods and integrate them with the invention herein to achieve the necessary purification of a particular antibody.

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about." Accordingly, unless indicated to the contrary, the numerical parameters set forth in the specification and attached claims are approximations that may vary depending upon the desired performance sought to be obtained by the present invention.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

The invention claimed is:

1. A method for purifying at least one non-aggregated antibody or at least one immunoreactive antibody fragment from an impure preparation containing said antibody or antibody fragment comprising the steps of (a) contacting the impure preparation with an apatite chromatography support, thereby binding the non-aggregated antibody or at least one immunoreactive antibody fragment to the apatite chromatography support and (b) eluting the antibody or immunoreactive antibody fragment by increasing the concentration of a monocarboxylate or monocarboxylate zwitterion in contact to the apatite chromatography support.

2. The method of claim 1, wherein the eluting comprises eluting the antibody or antibody fragment with a monocarboxylate.

3. The method of claim 2, wherein the monocarboxylate is acetate.

4. The method of claim 2, wherein the monocarboxylate is the primary eluting ion.

5. The method of claim 1, wherein the eluting comprises eluting the antibody or antibody fragment with a monocarboxylate zwitterion.

6. The method of claim 5, wherein the monocarboxylate zwitterion is glycine.

7. The method of claim 5, wherein the monocarboxylate zwitterion is the primary eluting ion.

8. The method of claim 5, wherein the monocarboxylic zwitterion possesses a pKa suitable for buffering in the pH range selected for the purification, is the primary buffering species, and is present at a concentration greater than 50 mM.

9. The method of claim 1, wherein the apatite chromatography support is hydroxyapatite.

10. The method of claim 1, wherein the apatite chromatography support is fluorapatite.

11. The method of claim 1, wherein the apatite chromatography support is in the support's native form.

12. The method of claim 1, wherein the apatite chromatography support is in a calcium-derivatized form.

13. The method of claim 1, wherein the apatite chromatography support is converted to its calcium derivatized form after the step of contacting the impure preparation with the apatite chromatography support.

14. The method of claim 1, wherein the apatite chromatography support is in equilibrium between its native form and a calcium-derivatized form.

15. The method of claim 1, wherein the elution is conducted in the presence of a nonionic organic polymer.

* * * * *